US008969791B2

(12) United States Patent
Mukaibatake (10) Patent No.: US 8,969,791 B2
(45) Date of Patent: Mar. 3, 2015

(54) QUANTITATIVE ANALYSIS METHOD USING MASS SPECTROMETER

(75) Inventor: Kazuo Mukaibatake, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 14/354,385

(22) PCT Filed: Oct. 28, 2011

(86) PCT No.: PCT/JP2011/074981
§ 371 (c)(1),
(2), (4) Date: Apr. 25, 2014

(87) PCT Pub. No.: WO2013/061466
PCT Pub. Date: May 2, 2013

(65) Prior Publication Data
US 2014/0299762 A1  Oct. 9, 2014

(51) Int. Cl.
*G01N 27/00* (2006.01)
*H01J 49/00* (2006.01)
*H01J 49/26* (2006.01)
*G01N 30/72* (2006.01)

(52) U.S. Cl.
CPC ......... *H01J 49/0031* (2013.01); *H01J 49/0036* (2013.01); *H01J 49/26* (2013.01); *G01N 30/72* (2013.01)
USPC ........ 250/252.1; 250/281; 250/282; 250/287; 250/288; 250/290; 702/23

(58) Field of Classification Search
CPC ..... H01J 49/025; H01J 49/40; H01J 49/0031; H01J 49/0009; H01J 49/0036; G01N 27/624; G01N 27/622

USPC ............. 250/282, 287, 281, 288, 290, 252.1; 702/23
See application file for complete search history.

(56) References Cited

U.S. PATENT DOCUMENTS

| 5,763,875 | A  | * | 6/1998 | Kaesdorf et al. | 250/287 |
| 2003/0089848 | A1 | * | 5/2003 | Holle et al. | 250/282 |
| 2007/0029477 | A1 | * | 2/2007 | Miller et al. | 250/290 |
| 2007/0176092 | A1 | * | 8/2007 | Miller et al. | 250/288 |
| 2007/0284521 | A1 | * | 12/2007 | Green et al. | 250/283 |
| 2008/0185513 | A1 | * | 8/2008 | Belov et al. | 250/288 |
| 2008/0237458 | A1 | * | 10/2008 | Wang | 250/282 |

(Continued)

FOREIGN PATENT DOCUMENTS

CA  2 713 082 A1  8/2009
EP  2 245 450  11/2010

(Continued)

*Primary Examiner* — David A Vanore
(74) *Attorney, Agent, or Firm* — Sughrue Mion, PLLC (57) ABSTRACT

In an MS unit, both an intensity of an ion having the highest intensity among the ions originating from a compound as the target of quantitative determination and an intensity of an isotopic ion are measured. A saturation detector determines whether or not digital data produced by an A/D converter from ion-intensity signals have reached a saturation level. A data selection controller selects the ion-intensity data showing the highest intensity when the signal is not saturated or the intensity data of the isotopic ion when the saturation has occurred or is probable to occur. When the latter data is selected, an ion intensity converter converts the intensity data into values corresponding to the intensity data of the highest-intensity ion by multiplying the intensity data by a factor calculated from a known isotopic abundance ratio.

8 Claims, 3 Drawing Sheets

(56) References Cited

U.S. PATENT DOCUMENTS

| | | | |
|---|---|---|---|
| 2010/0051799 A1* | 3/2010 | Makarov | 250/282 |
| 2010/0280764 A1* | 11/2010 | Thomson et al. | 702/23 |
| 2011/0042561 A1* | 2/2011 | Miller et al. | 250/282 |
| 2011/0095177 A1* | 4/2011 | Giannakopulos et al. | 250/282 |
| 2013/0035867 A1* | 2/2013 | De Moor et al. | 702/19 |
| 2013/0056627 A1* | 3/2013 | Verenchikov | 250/282 |
| 2013/0181125 A1* | 7/2013 | Guna et al. | 250/282 |
| 2013/0264474 A1* | 10/2013 | Kholomeev et al. | 250/287 |
| 2013/0317756 A1* | 11/2013 | Richardson et al. | 702/23 |
| 2014/0005970 A1* | 1/2014 | Richardson et al. | 702/104 |
| 2014/0346340 A1* | 11/2014 | Niehuis | 250/282 |

FOREIGN PATENT DOCUMENTS

| | | |
|---|---|---|
| JP | 9-318599 A | 12/1997 |
| JP | 2000-65797 A | 3/2000 |
| JP | 2010-71651 A | 4/2010 |
| JP | 2011-512534 A | 4/2011 |
| WO | 2009/103050 A1 | 8/2009 |

\* cited by examiner

QUANTITATIVE ANALYSIS METHOD USING MASS SPECTROMETER

CROSS REFERENCE TO RELATED APPLICATIONS

This application is a National Stage of International Application No. PCT/JP2011/074181, filed on Oct. 28, 2011, the contents of all of which are incorporated herein by reference in their entirety.

TECHNICAL FIELD

The present invention relates to a quantitative analysis method for measuring the intensity of an ion originating from a target compound using a mass spectrometer and for determining the quantity of the target compound based on the measured result, as well as a mass spectrometer using this method.

BACKGROUND ART

In a mass spectrometer, an ion having a specific mass-to-charge ratio m/z originating from a target compound in a sample is selectively detected and an ion intensity corresponding to the quantity of the ion is obtained. The ion intensity changes depending on the concentration (content) of the target compound. In the case of detecting the ion intensity of the same kind of ion, the higher the concentration of that compound is, the higher the ion intensity is, and vice versa. Accordingly, in a quantitative analysis using a chromatograph mass spectrometer consisting of a liquid chromatograph (LC) or gas chromatograph (GC) coupled to a mass spectrometer (MS), a plurality of standard samples which vary in the concentration of the target compound are previously subjected to the measurement to determine a calibration curve, i.e. an equation which represents the relationship between the concentration and the ion intensity, and this calibration curve is used to determine the concentration of the target compound in an unknown sample from an ion intensity obtained for the compound.

Normally, in the quantitative analysis, the mass spectrometer is operated in a selective ion monitoring (SIM) mode in which an ion having a mass-to-charge ratio m/z preset for the target compound is selectively detected and a mass chromatogram showing a temporal change in the intensity of the ion having the preset mass-to-charge ratio is obtained, as described in Patent Literature 1, for example. Subsequently, the area of a peak originating from the target compound and appearing on the mass chromatogram is calculated, and this peak area is used as the ion intensity on the calibration curve. Since a higher peak intensity gives a better S/N ratio of the peak area, a mass-to-charge ratio at which the ion intensity reaches the highest level is normally selected as the mass-to-charge ratio for quantitative determination among the mass-to-charge ratios of various ions originating from the target compound.

In the mass spectrometers available in recent years, ion-intensity signals obtained with a detector are converted into digital signals through an analogue-to-digital (A/D) converter and subjected to a waveform processing or other kinds of data processing. The dynamic range of commonly used A/D converters is no higher than approximately $10^6$. An input signal exceeding this upper limit causes the output to saturate and makes the data incorrect. Thus, the range in which the quantitative value (concentration) can be correctly obtained in a mass spectrometry is limited by the dynamic range of the A/D converter. Therefore, for example, when the system is tuned so as to enable A/D conversion of low ion-intensity signals for the purpose of determining an extremely small quantity, the ion-intensity signal for a high concentration of compound will exceed the dynamic rage of the A/D converter, so that the concentration cannot be measured at high levels of concentration.

CITATION LIST

Patent Literature

Patent Literature 1: JP 09-318599 A

SUMMARY OF INVENTION

Technical Problem

The present invention has been developed to solve the previously described problem, and its objective is to provide a quantitative analysis method by which the quantitative analysis can be performed over a wide range of concentrations without being limited by the dynamic range of an A/D converter or other processing circuits, as well as a mass spectrometer for performing a quantitative determination using the same method.

Solution to Problem

The first aspect of the present invention aimed at solving the previously described problem is a quantitative analysis method for determining the quantity of a target compound based on an ion intensity obtained by detecting an ion originating from the target compound using a mass spectrometer, the method including the following steps:

in a measurement of a sample containing the target compound, an ion intensity at a mass-to-charge ratio of an ion having the highest intensity among the ions originating from the target compound is detected, and additionally, an ion intensity at a mass-to-charge ratio of another ion having an intensity lower than the highest intensity by a predetermined proportion is detected;

a detection result of the ion intensity at the mass-to-charge ratio of the ion having the intensity lower than the highest intensity is converted into the ion intensity at the mass-to-charge ratio of the ion having the highest intensity; and in the case where the ion intensity at the mass-to-charge ratio of the ion having the highest intensity is expected or probable to exceed a saturation level, the ion intensity obtained by the aforementioned conversion is used to create a calibration curve for quantitative determination or to derive a quantitative value with reference to the calibration curve. The quantitative analysis method according to the first aspect of the present invention is designed for a quantitative determination using an intensity of a product ion generated by selecting and fragmenting an ion originating from a target compound.

The second aspect of the present invention aimed at solving the previously described problem is a mass spectrometer to be used for the mass analysis method according to the first aspect of the present invention, the mass spectrometer including:

a) a measurement executor for detecting, in a measurement of a sample containing a target compound, an ion intensity at the mass-to-charge ratio of an ion having the highest intensity among the ions originating from the target compound as well as an ion intensity at the mass-to-charge ratio of another ion having an intensity lower than the highest intensity by a predetermined proportion;

b) a conversion processor for converting a detection result of the ion intensity at the mass-to-charge ratio of the ion having the intensity lower than the highest intensity into the ion intensity at the mass-to-charge ratio of the ion having the highest intensity;

c) a saturation detector for detecting a state in which the ion intensity at the mass-to-charge ratio of the ion having the highest intensity has exceeded, or is probable to exceed, a saturation level; and d) a quantitative determination processor for performing a process of creating a calibration curve for quantitative determination or deriving a quantitative value with reference to the calibration curve, using the ion intensity at the mass-to-charge ratio of the ion having the highest intensity if the state of saturation or probable saturation has not been detected by the saturation detector, or using the ion intensity obtained through conversion by the conversion processor if the state of saturation or probable saturation has been detected by the saturation detector.

In conventional quantitative analysis methods using a mass spectrometer, attention is normally paid to only the ion having the highest intensity among the ions originating from a target compound, primarily from the viewpoint of the accuracy of the quantitative determination, and the intensity signal of that single ion is used to create a calibration curve and determine the quantity of the target compound of an unknown concentration with reference to the calibration curve. A quantitative analysis method which uses an ion other than the ion having the highest intensity among the ions originating from a target compound has also been known, in which case, once again, the intensity signal of that single ion is used to create a calibration curve and determine the quantity of the target compound of an unknown concentration with reference to the calibration curve. By contrast, in the quantitative analysis method according to the first aspect of the present invention and the mass spectrometer according to the second aspect of the present invention, not only the ion having the highest intensity among the ions originating from a target compound, but also the intensity or intensities of one or a plurality of ions whose mass-to-charge ratios are different from that of the ion having the highest intensity and whose intensities are lower than the highest intensity by predetermined proportions, are detected.

When a scan measurement is performed with the mass spectrometer, the ion intensities of interest can be obtained by performing the scan measurement over a mass-to-range ratio range which includes the mass-to-charge ratio of the ion having the highest intensity and the mass-to-charge ratio of the ion having an intensity lower than the highest intensity by a predetermined proportion. When a SIM measurement is performed with the mass spectrometer, the ion intensities of interest can be obtained by performing a SIM measurement in which the mass-to-charge ratio of the ion having the highest intensity and the mass-to-charge ratio of the ion having an intensity lower than the highest intensity by a predetermined proportion are set as the mass-to-charge ratios to be monitored.

As explained earlier, signal saturation occurs if an input signal (ion intensity) exceeds the upper limit of the dynamic range of an A/D converter or other processing circuits. However, even in the situation where the ion intensity at the mass-to-charge ratio of the ion having the highest intensity has exceeded the saturation level, the ion intensity at the mass-to-charge ratio of the ion having an intensity lower than the highest intensity by a predetermined proportion is adequately low with respect to the dynamic range and will not reach the saturation level. Accordingly, in the quantitative analysis method according to the first aspect of the present invention and the mass spectrometer according to the second aspect of the present invention, if the ion intensity at the mass-to-charge ratio of the ion having the highest intensity has actually exceeded or is likely to have exceeded the saturation level, or if the ion intensity has not yet reached the saturation level but is probable to exceed the level, a converted ion intensity obtained by converting the detection result of the ion intensity at the mass-to-charge ratio of the ion having an intensity lower than the highest intensity is used in the process of creating a calibration curve or deriving a quantitative value with reference to the calibration curve, instead of the ion intensity at the mass-to-charge ratio of the ion having the highest intensity. Conversely, if the ion intensity at the mass-to-charge ratio of the ion having the highest intensity is adequately low with respect to the dynamic range and is unlikely to reach the saturation level, this ion intensity can be used to create the calibration curve or derive the quantitative value. Thus, the mass-to-charge ratio of the ion intensity to be used for creating a calibration curve or deriving a quantitative value is appropriately selected according to whether or not the ion intensity at the mass-to-charge ratio of the ion having the highest intensity has exceeded, or is probable to exceed, the saturation level.

In a preferable mode of the first and second aspects of the present invention, the ion having the highest intensity among the ions originating from the target compound is a principal ion composed of principal isotopes, while the ion having an intensity lower than the highest intensity by a predetermined proportion is a subsidiary ion containing an isotope other than the principal isotopes. In this case, it is possible to use a plurality of subsidiary ions having different mass-to-charge ratios rather than a single subsidiary ion.

Normally, in a quantitative analysis, the composition of the target compound is previously known, and the isotopic abundance ratios of the constituent elements of the compound are also known. Accordingly, the abundance ratio between the principal ion and the subsidiary ion originating from the target compound can be determined by theoretical calculation, and the ratio between the intensity of the subsidiary ion and that of the principal ion should be equal to the abundance ratio. Therefore, by using the theoretically calculated abundance ratio, it is possible to convert a detection result of the ion intensity at the mass-to-charge ratio of the ion having the intensity lower than the highest intensity into the ion intensity at the mass-to-charge ratio of the ion having the highest intensity, as described above.

Even if the abundance ratio between the principal ion and the subsidiary ion cannot be determined by theoretical calculation, the aforementioned conversion can be performed using a ratio between the intensity of a peak corresponding to the principal ion and that of a peak corresponding to the subsidiary ion, the ratio determined by an actual measurement of a sample.

Instead of the ion intensity of the subsidiary ion containing an isotope other than the principal isotopes, an ion intensity at a position on the mass-to-charge-ratio axis displaced from (i.e. at a mass-to-charge ratio displaced from) the peak top of the peak formed by the ion having the highest intensity among the ions originating from the target compound on a mass spectrum (typically, an ion intensity at a position within the rising or falling slope section of the peak) may be used as the ion intensity at the mass-to-charge ratio of the ion having an intensity lower than the highest intensity by a predetermined proportion.

Ideally, one peak appearing on a mass spectrum should be a single line. However, what is actually obtained is a profile data with a certain width. The peak width depends on the state of tuning or setting of the parameters of the components in the system. Accordingly, provided that the state of tuning or setting of the parameters is identical, the peak width will be the same and it is possible to calculate the position (i.e. mass-to-charge ratio) on the slope section of the peak at which the intensity is lower than the peak-top intensity of the peak by a predetermined proportion. Using this fact, it is possible to perform quantitative determination by the quantitative analysis method according to the first aspect of the present invention using a single peak even if no isotopic peak exists or the peak-top intensities of the isotopic peaks are too low.

In the case of determining the quantity of a target compound with a chromatograph mass spectrometer consisting of a chromatograph (e.g. LC or GC) coupled with a mass spectrometer, the quantity is normally determined using the area of a peak originating from the target compound and appearing on a mass chromatogram or total ion chromatogram obtained for an ion originating from the target compound. Accordingly, in the case where the quantitative analysis method according to the first aspect of the present invention is applied in a chromatograph mass spectrometer, the calibration curve may be a curve representing a relationship between the chromatogram peak area originating from the target compound and the compound concentration.

Advantageous Effects of the Invention

With the quantitative analysis method according to the first aspect of the present invention and the mass spectrometer according to the second aspect of the present invention, it is possible to create a correct calibration curve and derive a quantitative value with reference to the calibration curve even if an ion-intensity signal obtained for a high concentration of target compound becomes saturated due to the limitation on the dynamic range of a processing circuit (such as an A/D converter for digitizing signals obtained with an ion detector). Thus, a quantitative analysis covering a wide range of concentrations can be performed without being limited by the dynamic range of the processing circuit.

DESCRIPTION OF EMBODIMENTS

The principle of the quantitative analysis method according to the present invention is initially described with reference to FIGS. 2 and 3.

Figure 2:
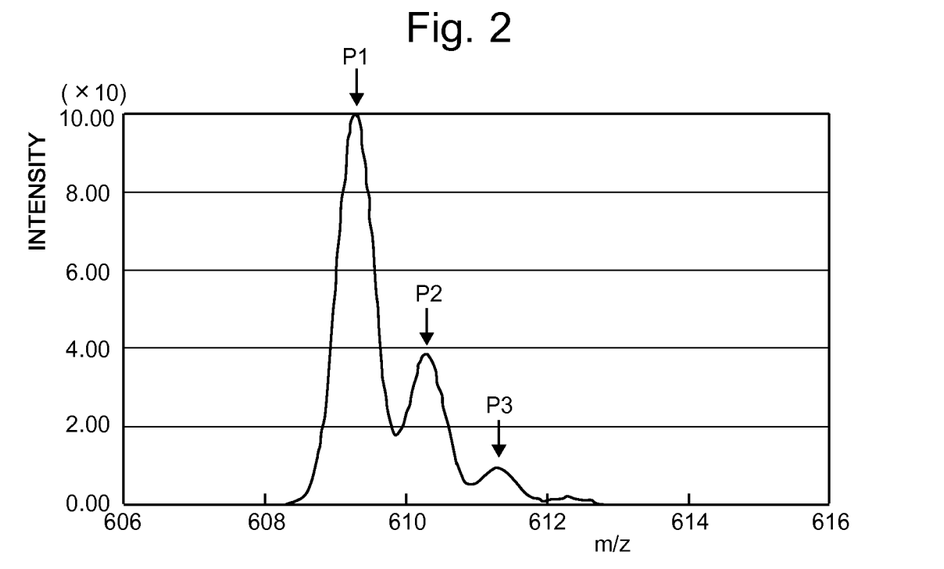
FIG. 2 shows one example of the mass spectrum (profile data) obtained.

FIG. 2 shows one example of the mass spectrum (profile data) obtained by a mass spectrometry of reserpine ($C_{33}H_{40}N_2O_9$) in the positive ionization mode. As shown, a principal peak P1 having the highest ion intensity occurs at m/z 609.3. This principal peak P1 corresponds to the peak of the molecular ion ($[M+H]^+$) of the reserpine composed of only the principal isotopes. Additionally, two subsidiary peaks P2 and P3, which are isotopic peaks of reserpine containing an isotope other than the principal isotopes, are present at m/z 610.3 and m/z 611.3 displaced from the principle peak P1 by 1 Da and 2 Da, respectively.

The natural isotopic abundance ratios of the constituent elements of reserpine, i.e. carbon (C), hydrogen (H), nitrogen (N) and oxygen (O), are generally known. For example, carbon has two isotopes, $^{12}C$ and $^{13}C$, whose mass-to-charge ratios are 12 and 13, respectively. Their abundance ratio is commonly known as $^{12}C:^{13}C=98.9\%:1.10\%$. Similar information is also available for the other elements. Accordingly, the isotopic abundance ratios of the aforementioned three kinds of molecular ions of reserpine having different mass-to-charge ratios can be easily calculated from the chemical composition formula of reserpine and the isotopic abundance ratio of each element. Since the ion intensity at the peak top of each isotopic peak on the mass spectrum reflects the amount of ions, the ion-intensity ratio is equal to the abundance ratio of the isotopic compounds. Therefore, it is easy to calculate the ratio of the ion intensity of each subsidiary peak P2 or P3 to that of the principal peak P1. Specifically, the ion intensity of the subsidiary peak P2 at m/z 610.3 is 38.4% of that of the principal peak P1, while the ion intensity of the subsidiary peak P3 at m/z 611.3 is 9.0% of that of the principal peak P1.

Consider the case where analogue detection signals produced by an ion detector are converted into digital data through an A/D converter whose upper limit of the input dynamic range is $1 \times 10^6$. An input of the ion-detection signal exceeding this upper limit causes output data to exceed the saturation level. FIG. 2 shows the result of a measurement in which the reserpine concentration is not so high as to cause such signal saturation. By contrast, if the measurement is performed on a high concentration of reserpine that causes the ion intensity to reach, for example, as high as $2 \times 10^6$, the principal peak P1 on the mass spectrum has its peak top cut off, as shown in FIG. 3. Naturally, if the ion intensity at m/z 609.3 corresponding to this principal peak P1 is used as the basis for creating the calibration curve and determining the quantity, the determined quantity cannot be correct.

Figure 3:
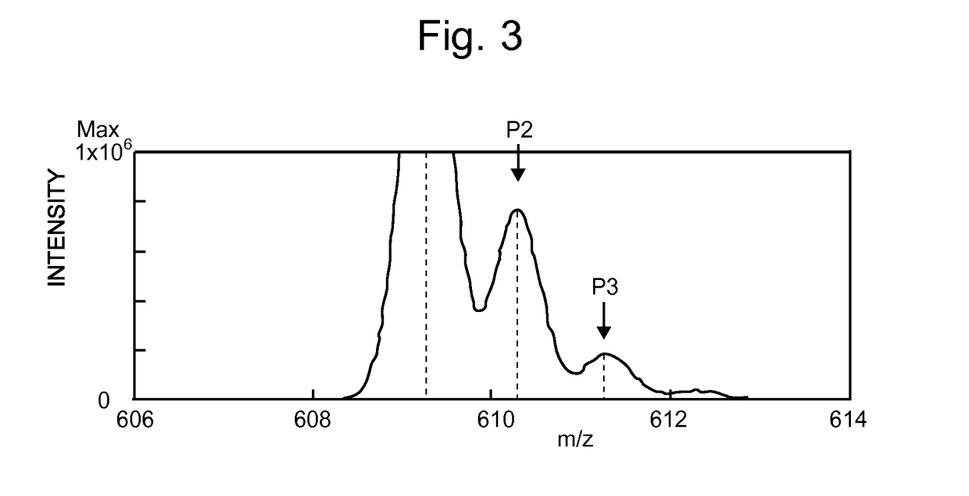
FIG. 3 shows another example of the mass spectrum (profile data) obtained.

On the other hand, the subsidiary peaks P2 and P3 at m/z 610.3 and m/z 611.3 are lower than the saturation level even in the case of FIG. 3. That is to say, even in the situation where the principal peak P1 exceeds the saturation level, the ion intensities of the subsidiary peaks P2 and P3 are still available for creating the calibration curve and determining the quantity. Accordingly, in the quantitative analysis method according to the present invention, in the situation where the principal peak P1 exceeds the saturation level, a subsidiary peak whose ion intensity is inherently lower than that of the principal peak P1 (e.g. the subsidiary peak P3 at m/z 611.3) is used for the quantitative determination. That is to say, the ion intensity $I_{P3}$ at the peak top of the subsidiary peak P3 at m/z 611.3 is initially determined. As explained earlier, the ion intensity of the subsidiary peak P3 should theoretically be 9.0% of that of the principal peak P1. Accordingly, the ion intensity $I_{P3}$ of the subsidiary peak P3 is converted into that of the principal peak P1 at m/z 609.3 by performing a calculation of $I_{P3} \times (1/0.09)$ or $I_{P3} \times 11.1$. In other words, when the ion intensity of the principal peak P1 cannot be directly determined, a pseudo or virtual ion intensity of the principal peak P1 is calculated. It should be noted that, when the principal peak P1 does not exceed the saturation level as shown in FIG. 2, the ion intensity of the principal P1 should be used for the creation of the calibration curve and the quantitative calculation, since the noise level can be regarded as approximately constant, and therefore, a peak with a higher ion intensity has a higher S/N ratio.

Thus, when the principal peak P1 does not exceed the saturation level, the task of creating the calibration curve and calculating the quantity is performed using the ion intensity of the principal peak P1, and when the principal peak P1 exceeds the saturation level, the aforementioned task is performed using a value obtained by converting the ion intensity of the subsidiary peak P3 (or P2) having an inherently low intensity according to the isotopic abundance ratio. By this technique, the concentration range covered by the quantitative analysis can be effectively expanded to approximately ten times the dynamic range of the A/D converter.

Figure 1:
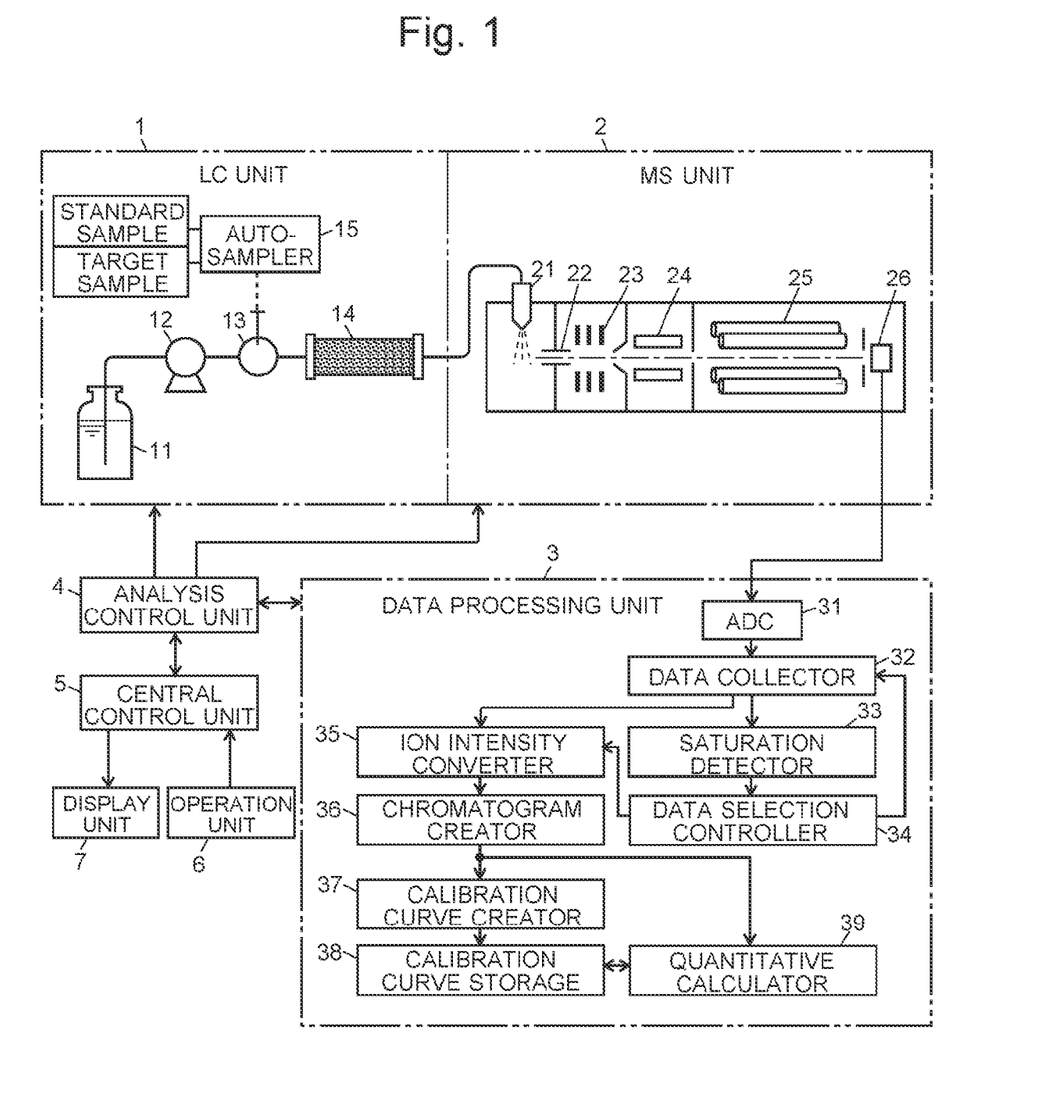
FIG. 1 is a schematic configuration diagram of a liquid chromatograph mass spectrometer (LC/MS) as one embodiment of the mass spectrometer for carrying out the quantitative analysis method according to the present invention.

One embodiment of the LC/MS for carrying out the quantitative analysis based on the previously described principle is hereinafter described with reference to the attached drawings. FIG. 1 is a schematic configuration diagram of the present LC/MS.

In an LC unit 1, a liquid-sending pump 12 draws a mobile phase from a mobile phase container 11 and supplies it at a preset flow rate. An auto-sampler 15 selects one of the prepared standard samples and a target sample (or possibly, a plurality of target samples). An injector 13 injects the selected sample into the stream of mobile phase at a predetermined timing. The injected sample is carried by the mobile phase, to be introduced into a column 14. While passing through the column 14, the various compounds in the sample are temporally separated and eluted.

In an MS unit 2, the eluent supplied from the column outlet is electro-sprayed from an ionization probe 21 into an ionization chamber maintained at approximately atmospheric pressure, whereby the compounds in the eluate are ionized. The generated ions are conveyed through a desolvation pipe 22 as well as two ion guides 23 and 24, to be introduced into a quadrupole mass filter 25 provided in a high-vacuum atmosphere. The ions having a specific mass-to-charge ratio m/z corresponding to the voltage (DC voltage+RF voltage) applied to the quadrupole mass filter 25 from a voltage source (not shown) are selectively allowed to pass through the filter 25 and arrive at an ion detector 26. The ion detector 26 generates detection signals corresponding to the amount of ions which have reached the detector 26.

A data processing unit 3 includes an A/D converter (ADC) 31 for digitizing analogue detection signals as well as other functional blocks, such as a data collector 32, a saturation detector 33, a data selection controller 34, an ion intensity converter 35, a chromatogram creator 36, a calibration curve creator 37, a calibration curve storage section 38 and a quantitative calculator 39. An analysis control unit 4 controls the operations of the LC unit 1, the MS unit 2 and the data processing unit 3 according to the instructions from a central control unit 5. The central control unit 5, to which an operation unit 6 (such as a keyboard) and a display unit 7 (such as a monitor display) are connected, provides an input/output interface as well as supervises the general control of the system. At least a portion of the functions of the central control unit 5, the analysis control unit 4 and the data processing unit 3 can be realized by using a personal computer provided as hardware resources and executing a dedicated controlling and processing software program installed on the computer.

A process of determining the quantity of a known kind of target compound is hereinafter described as an example of the operation of the LC/MS according to the present embodiment. Initially, a calibration curve is created using a plurality of standard samples containing the target compound. In the present case, since the kind of target compound is known, the mass-to-charge ratio of the ion having the highest intensity and those of the isotopic ions are also known. For example, if the previously mentioned reserpine is the target compound, it is previously known that the mass-to-charge ratio of the ion having the highest intensity is 609.3, while the mass-to-charge ratios of the isotopic ions are 610.3 and 611.3. Furthermore, as already described, the abundance ratios of those isotopic ions can also be determined by theoretical calculation. Accordingly, by operating the operation unit 6, a user (analysis operator) sets the measurement mode of the MS unit 2 to the SIM mode and designates the three m/z values of 609.3, 610.3 and 611.3 as the mass-to-charge ratios to be monitored. The user also enters the abundance ratios of the isotopic ions through the operation unit 6 as one of the parameters for the data processing.

A standard sample containing a known concentration of target compound is injected from the injector 13 into the mobile phase. In the MS unit 2, the SIM measurement is repeatedly performed for the mass-to-charge ratios which have been set in the previously described manner. In the data processing unit 3, the data collector 32 collects data corresponding to the ion intensity at each of the three mass-to-charge ratios and at preset intervals of sampling time. When the target compound begins to emerge in the eluate exiting from the column outlet 14, the ion intensity begins to increase with time at any of the aforementioned mass-to-charge ratios and then gradually decreases after reaching the maximum intensity. By plotting the ion-intensity data at a specific mass-to-charge ratio (e.g. m/z 609.3) with respect to time, a mass chromatogram can be obtained.

If the ion-intensity signal fed to the A/D converter 31 exceeds the upper limit of the input dynamic range of the A/D converter 31, the output data exceeds the saturation level. In this situation, for example, the A/D converter 31 produces the same maximum-value data regardless of the level of the input signal. The saturation detector 33 determines whether or not the time-series data collected by the data collector 32 has entered a preset margin from the maximum-value data corresponding to the signal saturation. If the data has been found to have entered the margin, it is determined that the signal has been saturated. Thus, the situation which is most likely to cause signal saturation can be detected before the signal is actually saturated.

Figure 4:
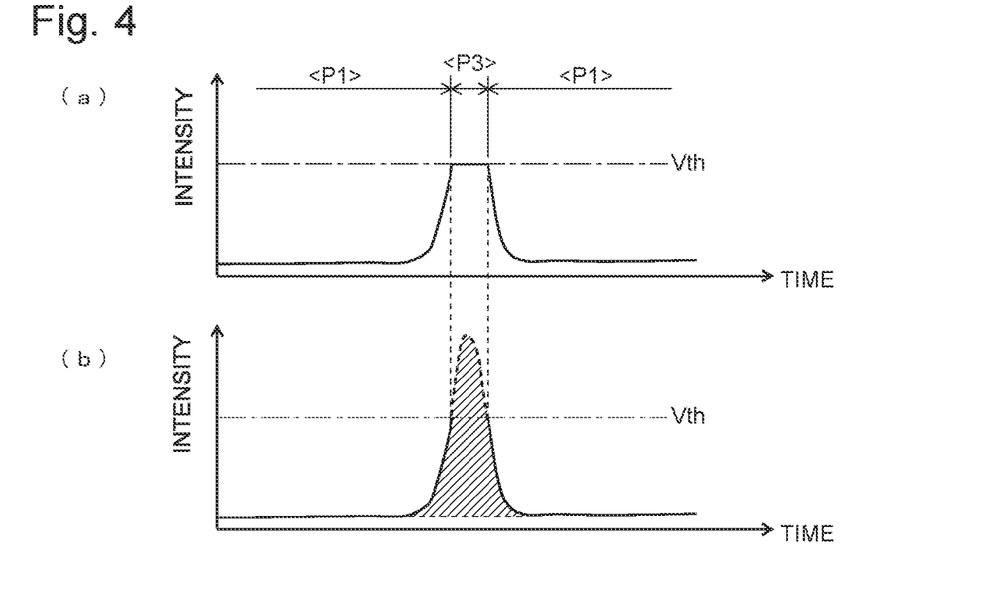
FIG. 4 shows one example of the mass chromatogram obtained.

Such a signal saturation occurs when the concentration of the target compound is high. Meanwhile, as explained earlier, the ion intensity changes with time due to the separation characteristics of the LC unit 1. Therefore, for example, the mass chromatogram will be as shown in FIG. 4(a): a chromatogram peak originating from the target compound initially rises until the ion intensity reaches a threshold Vth (which is determined by the upper limit of the input dynamic range of the A/D converter 31), after which the chromatogram peak remains at the saturation level and subsequently begins to fall when the true value of the ion intensity becomes lower than the threshold Vth. In the example of FIG. 4(a), the saturation detector 33 distinguishes between the time range <P1> and the time range <P3> period and sends the corresponding signals to the data selection controller 34.

The data selection controller 34 controls the data collector 32 so that the ion-intensity data at m/z 609.3, which gives the highest ion intensity, are selected as output data during the time ranges <P1> while the ion-intensity data at m/z 611.3, at which the ion intensity is inherently low, are selected as output data during the time range <P3>. Alternatively, the ion-intensity data at m/z 610.3 may be selected as output data for the time range <P3>. The data thus selected by the data collector 32 are sequentially sent to the ion intensity converter 35, in which the data received in the time range <P1> are directly forwarded as output data while the data received in the time range <P3> (i.e. the ion intensity at m/z 611.3) are multiplied by a conversion factor corresponding to the abundance ratio of the isotopic ions (in the present example, 1/0.09=11.1) to obtain intensity values corresponding to the ion intensity at m/z 609.3 as output data.

The chromatogram creator 36 receives the data from the ion intensity converter 35 and plots the data with respect to time to create a mass chromatogram. As just described, the data obtained by the conversion in the ion intensity converter 35 are available in the time range <P3>. Using those pieces of data, the chromatogram creator 36 creates a mass chromatogram in which a pseudo-peak portion is formed in the time range <P3>, as shown in FIG. 4(b). It can be said that the pseudo-peak portion is substantially correct, since the theoretical calculation of the isotopic abundance ratio is correct, and furthermore, since the conditions which affects the ion-intensity data (e.g. the ionization efficiency in the ion source or the ion-detection sensitivity in the ion detector 26) can be regarded as identical within an extremely narrow range of mass-to-charge ratios, such as a few Da or smaller.

Figure 5:
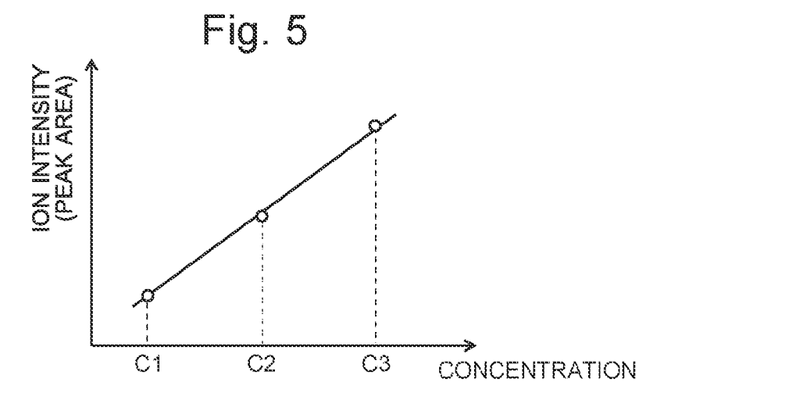
FIG. 5 shows one example of the calibration curve created.

The calibration curve creator 37 detects a peak originating from the target compound on the mass chromatogram, and calculates the area of that peak (the shaded area in FIG. 4(b)). After the plurality of standard samples having different concentrations of the target compound are individually subjected to the measurement in the same manner and the peak area on the chromatogram is calculated for each measurement result, the calibration curve creator 37 creates a calibration curve representing the relationship between the concentration and the peak area, as shown in FIG. 5, and stores the curve in the calibration curve storage section 38. This calibration curve is used as the reference data for determining the quantity of the target compound (which, in the present case, is reserpine).

When an unknown concentration of the target compound contained in the target sample needs to be determined, the previously described measurement is similarly performed on the target sample, and the peak area originating from the target compound on the mass chromatogram is calculated. Naturally, in this measurement, if the ion-intensity signal fed to the A/D converter 31 exceeds the upper limit of the input dynamic range, a portion of the peak on the mass chromatogram will be created from the data obtained by converting the ion-intensity data at m/z 611.3 (or m/z 610.3) instead of the ion-intensity data at m/z 609.3. Thus, a high-accuracy quantitative determination can be achieved even in the case where the concentration of the compound is so high that the ion intensity exceeds the upper limit of the input dynamic range of the A/D converter 31.

The description of the previous embodiment has assumed that the mass chromatogram is created almost in real time, concurrently with the measurement, by performing the data selection and conversion based on the obtained ion-intensity data. It is evidently possible to temporarily store the entire set of data obtained through the measurement in a memory area in the data collector 32 and perform a similar process in a batch mode after the measurement.

The description of the previous embodiment has also assumed that a SIM measurement is performed by the MS unit 2. It is also possible to collect data by a scan measurement which covers a range of mass-to-charge ratios including those of the target ions. That is to say, any measurement mode can be used as long as both the ion intensity at the mass-to-charge ratio of an ion having the highest intensity and the ion intensity of an isotopic ion whose intensity is inherently lower than the highest intensity can be measured, as in the case of the SIM or scan measurement mode.

In the case where the MS unit 2 is a triple quadrupole mass spectrometer or another type of mass spectrometer capable of MS/MS analysis, the previously described process for quantitative determination can also be performed on an ion-intensity signal obtained by detecting product ions. For example, in the case of determining the quantity of reserpine by an MS/MS analysis in a selective reaction monitoring (SRM) measurement mode, a normal procedure is as follows: A collision induced dissociation (CID) or similar process using the ion of m/z 609.3 having the highest intensity as the precursor ion is performed; the thereby generated product ion of m/z 195 is selectively detected; and the quantitative determination is performed using the ion intensity of the product ion. In this case, if the intensity signal of the product ion of m/z 195 exceeds the upper limit of the input dynamic range of the A/D converter 31, the output data exceeds the saturation level and the quantity cannot be correctly determined. In such a case, a correct quantitative determination with no saturation of the signal can be achieved according the previously described method by performing the CID or similar process using the ion of m/z 611.3 originating from an isotopic peak as the precursor ion and selectively detecting the thereby generated product ion of m/z 197.

In the previous embodiment, the mass-to-charge ratio of an ion composed of only the principal isotopes is used as the mass-to-charge ratio of the ion having the highest intensity, while the mass-to-charge ratio of an isotopic ion containing an element other than the principal isotopes is used as the mass-to-charge ratio of the ion which should serve as a substitute for the former mass-to-charge ratio when the signal corresponding to the highest intensity is saturated. However, the latter does not need to be a mass-to-charge ratio corresponding to a peak originating from an isotopic ion; it may be the mass-to-charge ratio of any ion having an intensity lower than the highest intensity by a predetermined proportion. For example, it is possible to measure an ion intensity at a position displaced from the peak top of the ion having the highest intensity among the ions originating from the target compound, i.e. at a mass-to-charge ratio corresponding to a position in the middle of the rising or falling slope section of the peak.

Figure 6:
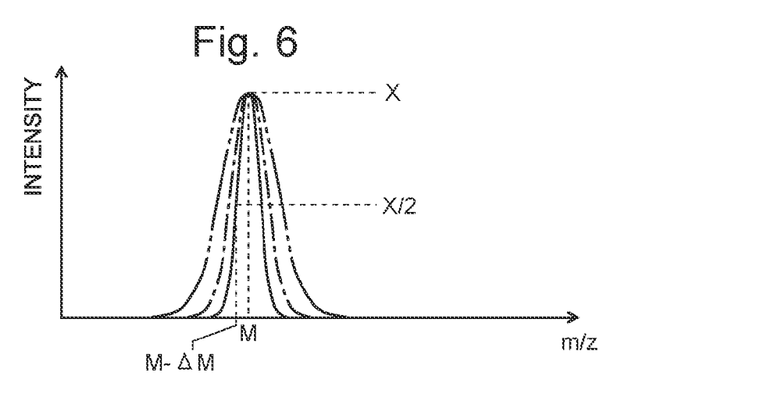
FIG. 6 is a diagram for explaining another example of the quantitative analysis method according to the present invention.

This idea is specifically as follows: When an ion of mass-to-charge ratio M is selectively detected in a mass spectrometer, the actually observed peak has a certain width around the target mass-to-charge ratio M, as shown in FIG. 6. This peak width is associated with the mass-resolving power and depends on the state of tuning or setting of various control parameters used in the mass spectrometer, such as a voltage applied to a quadrupole mass filter. Once the tuning or setting of the control parameters is completed, the peak width is determined. Ideally, the peak takes the form of a Gaussian distribution. Therefore, based on the already determined peak width, it is possible to find the mass-to-charge ratio at which the intensity is lower than the peak-top intensity X of the peak by a predetermined proportion, or to find the amount of displacement of that mass-to-charge ratio. In FIG. 6, M-ΔM indicates the mass-to-charge ratio at which the intensity in the peak waveform having the smallest width in the figure is equal to one half of the peak-top intensity X.

Thus, under the condition that the state of tuning or setting of the control parameters is identical, the ion intensity at a mass-to-charge ratio which is displaced from the peak top by a predetermined amount is always lower than the peak-top intensity by a predetermined proportion and hence can be used instead of the ion intensity of the previously described isotopic ion. By this method, the concentration can be correctly determined over a broad range even if the abundance ratio of a compound containing an isotope other than the principal isotopes is extremely low and the intensity of the isotopic ion originating from that compound is extremely low.

It should be noted that the present invention is not limited the previously described embodiment or its variations, and any change, addition or modification appropriately made within the spirit of the present invention will evidently fall within the scope of claims of the present patent application.

REFERENCE SIGNS LIST

1 . . . Liquid Chromatograph (LC) Unit
11 . . . Mobile Phase Container
12 . . . Liquid-Sending Pump
13 . . . Injector
14 . . . Column
15 . . . Auto-Sampler
2 . . . Mass Spectrometer (MS) Unit
21 . . . Ionization Probe
22 . . . Desolvation Pipe
23, 24 . . . Ion Guide
25 . . . Quadrupole Mass Filter
26 . . . Ion Detector
3 . . . Data Processor
31 . . . A/D Converter
32 . . . Data Collector
33 . . . Saturation Detector
34 . . . Data Selection Controller
35 . . . Ion Intensity Converter
36 . . . Chromatogram Creator
37 . . . Calibration Curve Creator
38 . . . Calibration Curve Storage Section
39 . . . Quantitative Calculator
4 . . . Analysis Control Unit
5 . . . Central Control Unit
6 . . . Operation Unit
7 . . . Display Unit

The invention claimed is:

1. A quantitative analysis method for determining a quantity of a target compound based on an ion intensity obtained by detecting an ion originating from the target compound using a mass spectrometer, the method using an intensity of a product ion obtained by selecting and fragmenting an ion originating from a target compound, and the method including following steps:

in a measurement of a sample containing a target compound, an ion intensity at a mass-to-charge ratio of an ion having a highest intensity among product ions obtained by performing an $MS^n$ analysis using different kinds of ions originating from the target compound as precursor ions is detected, and additionally, an ion intensity at a mass-to-charge ratio of another ion having an intensity lower than the highest intensity by a predetermined proportion is detected;

a detection result of the ion intensity at the mass-to-charge ratio of the ion having the intensity lower than the highest intensity is converted into the ion intensity at the mass-to-charge ratio of the ion having the highest intensity; and in a case where the ion intensity at the mass-to-charge ratio of the ion having the highest intensity is expected or probable to exceed a saturation level, the ion intensity obtained by the aforementioned conversion is used to create a calibration curve for quantitative determination or to derive a quantitative value with reference to the calibration curve.

2. The quantitative analysis method using a mass spectrometer according to claim 1, wherein:

the ion having the highest intensity is a principal ion composed of principal isotopes, while the ion having an intensity lower than the highest intensity by a predetermined proportion is a subsidiary ion containing an isotope other than the principal isotopes.

3. The quantitative analysis method using a mass spectrometer according to claim 2, wherein:

the predetermined proportion is an abundance ratio between the principal ion and the subsidiary ion, the abundance ratio being calculated based on a known isotopic abundance ratio, and the aforementioned conversion is performed using the abundance ratio determined by theoretical calculation.

4. The quantitative analysis method using a mass spectrometer according to claim 2, wherein:

the aforementioned conversion is performed using a ratio between an intensity of a peak corresponding to the principal ion and that of a peak corresponding to the subsidiary ion, the ratio being determined by an actual measurement of a sample.

5. The quantitative analysis method using a mass spectrometer according to claim 1, wherein:

the intensity of the ion having the highest intensity, and the intensity of the ion having an intensity lower than the highest intensity by a predetermined proportion, are obtained by performing a selective reaction monitoring measurement in which the mass-to-charge ratios of these two ions are set as the ions to be detected.

6. The quantitative analysis method using a mass spectrometer according to claim 1, wherein:

the intensity of the ion having the highest intensity, and the intensity of the ion having an intensity lower than the highest intensity by a predetermined proportion, are obtained by performing a scan measurement over a range of mass-to-charge ratios including the mass-to-charge ratios of these two ions.

7. The quantitative analysis method using a mass spectrometer claim 1, wherein:

the mass spectrometer is used for performing a mass spectrometry of compounds separated by a chromatograph, and the calibration curve represents a relationship between a chromatogram peak area originating from a target compound and a compound concentration.

8. A mass spectrometer to be used for the mass analysis method according to claim 1, comprising:

a) a measurement executor for detecting, in a measurement of a sample containing a target compound, an ion intensity at the mass-to-charge ratio of an ion having a highest intensity among product ions obtained by performing an $MS^n$ analysis using different kinds of ions originating from the target compound as precursor ions as well as an ion intensity at a mass-to-charge ratio of another ion having an intensity lower than the highest intensity by a predetermined proportion;

b) a conversion processor for converting a detection result of the ion intensity at the mass-to-charge ratio of the ion having the intensity lower than the highest intensity into the ion intensity at the mass-to-charge ratio of the ion having the highest intensity;
c) a saturation detector for detecting a state in which the ion intensity at the mass-to-charge ratio of the ion having the highest intensity has exceeded, or is probable to exceed, a saturation level; and
d) a quantitative determination processor for performing a process of creating a calibration curve for quantitative determination or deriving a quantitative value with reference to the calibration curve, using the ion intensity at the mass-to-charge ratio of the ion having the highest intensity if the state of saturation or probable saturation has not been detected by the saturation detector, or using the ion intensity obtained through conversion by the conversion processor if the state of saturation or probable saturation has been detected by the saturation detector.

* * * * *